US006454097B1

(12) United States Patent
Blanco

(10) Patent No.: US 6,454,097 B1
(45) Date of Patent: Sep. 24, 2002

(54) PRIORITIZED FIRST AID KIT

(76) Inventor: Juan Carlos Aceves Blanco, 2300 Nacogdoches #250-L, San Antonio, TX (US) 78209

( * ) Notice: Subject to any disclaimer, the term of this patent is extended or adjusted under 35 U.S.C. 154(b) by 0 days.

(21) Appl. No.: 09/567,813

(22) Filed: May 9, 2000

(51) Int. Cl.[7] .............................................. B65D 69/00
(52) U.S. Cl. ..................... 206/570; 206/523; 206/459.5
(58) Field of Search ................... 206/370, 438, 206/459.5, 523, 570–572; 16/DIG. 24, DIG. 25, DIG. 41; 24/453, 607; 220/522, 524, 845, 848

(56) References Cited

U.S. PATENT DOCUMENTS

| | | | |
|---|---|---|---|
| 611,136 A | | 9/1898 | Mason |
| 1,480,865 A | | 1/1924 | Slade |
| 1,644,830 A | | 10/1927 | Henderson |
| 2,999,583 A | | 9/1961 | Mancini |
| 4,828,113 A | | 5/1989 | Friedland et al. |
| 4,863,062 A | * | 9/1989 | Holliday ..................... 220/845 |
| 4,917,238 A | * | 4/1990 | Schumacher ................ 206/570 |
| 5,011,020 A | | 4/1991 | Stevens et al. |
| 5,207,303 A | | 5/1993 | Oswalt et al. |
| 5,515,974 A | | 5/1996 | Higson |
| 5,547,079 A | | 8/1996 | Pino |
| 5,638,577 A | | 6/1997 | Gooding et al. |
| 5,848,700 A | | 12/1998 | Horn |
| 5,931,304 A | | 8/1999 | Hammond |
| 6,019,223 A | * | 2/2000 | Harftst ........................ 206/523 |
| 6,286,682 B1 | * | 9/2001 | d'Arbelles .................. 206/570 |

OTHER PUBLICATIONS

Johnson & Johnson Advertisement, *Good Housekeeping*, May 1999, published Apr. 13, 1999.
Description of First Aid Kit Offered for Sale to Zee Medical, Inc., 1995, California, USA.

* cited by examiner

*Primary Examiner*—Luan K. Bui
(74) *Attorney, Agent, or Firm*—Loeffler, Jonas & Tuggey, LLP

(57) ABSTRACT

This invention is directed to an improved first aid kit having a foam case with a plurality of integral, internal compartments containing medical supplies for treating a number of medical emergencies. Each compartment is directed to a specific type of medical emergency, which is identified by indicia on the lid of each compartment. The indicia on the compartment lids preferably contain simple, eye-catching, color-coded graphical illustrations of the particular medical emergencies so that an unskilled person can readily ascertain the appropriate compartments to access in an emergency situation. Additionally, the various medical emergencies are preferably prioritized in order of life threatening severity. The kit is buoyant and also functions as a personal flotation device. The compartment lids of the present invention are preferably installed with special hinges having ribs that are embedded in the foam of the case to help prevent the hinges from coming loose. Also, a preferred case comprises two interfitting modules that form a watertight seal. The two modules are connected with hinges that are fastened to the foam with special barbed fasteners. The two modules are also held together with a pair of straps that are fastened to the foam with similar barbed fasteners. A handle is fastened to one of the foam modules with a unique snap-in fastener.

27 Claims, 20 Drawing Sheets

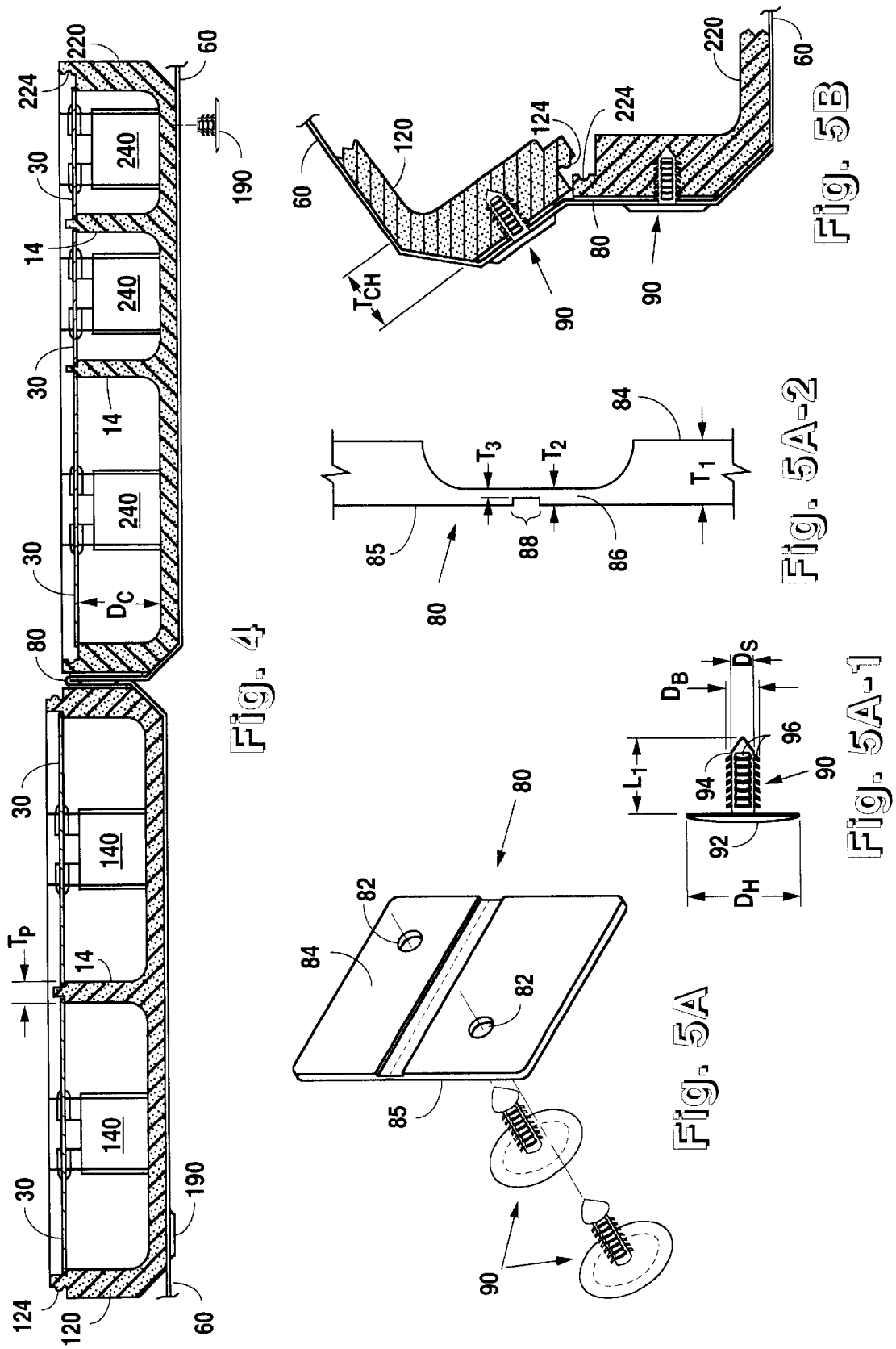

Fig. 15
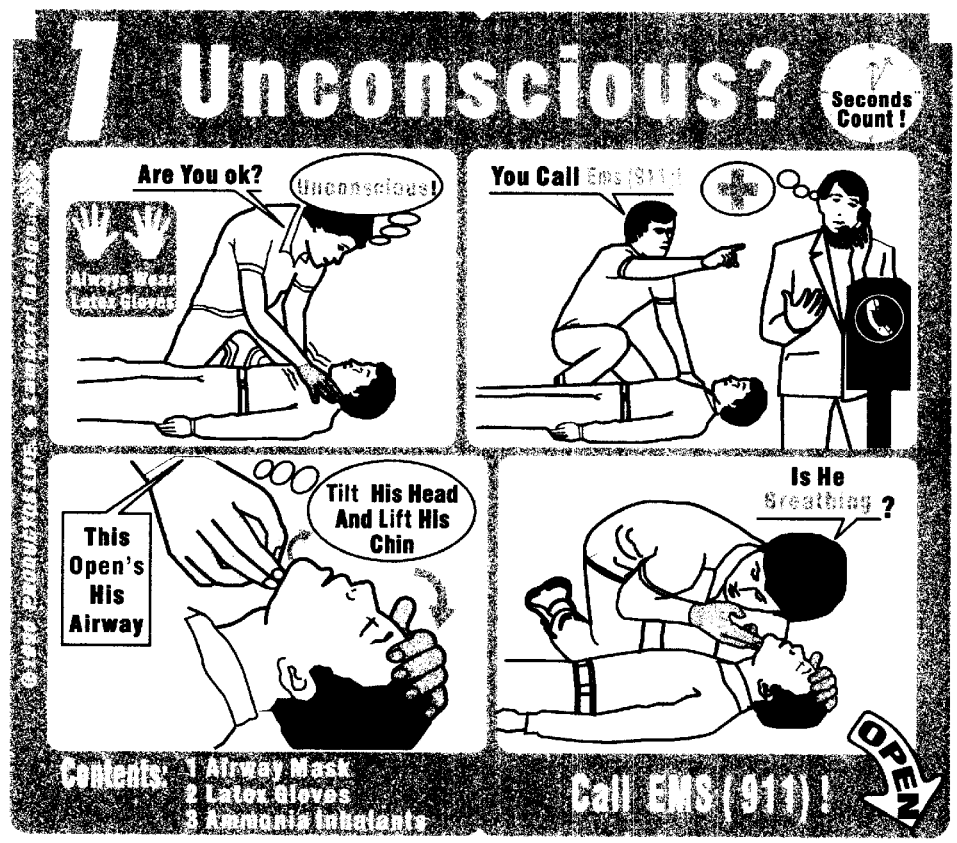
T
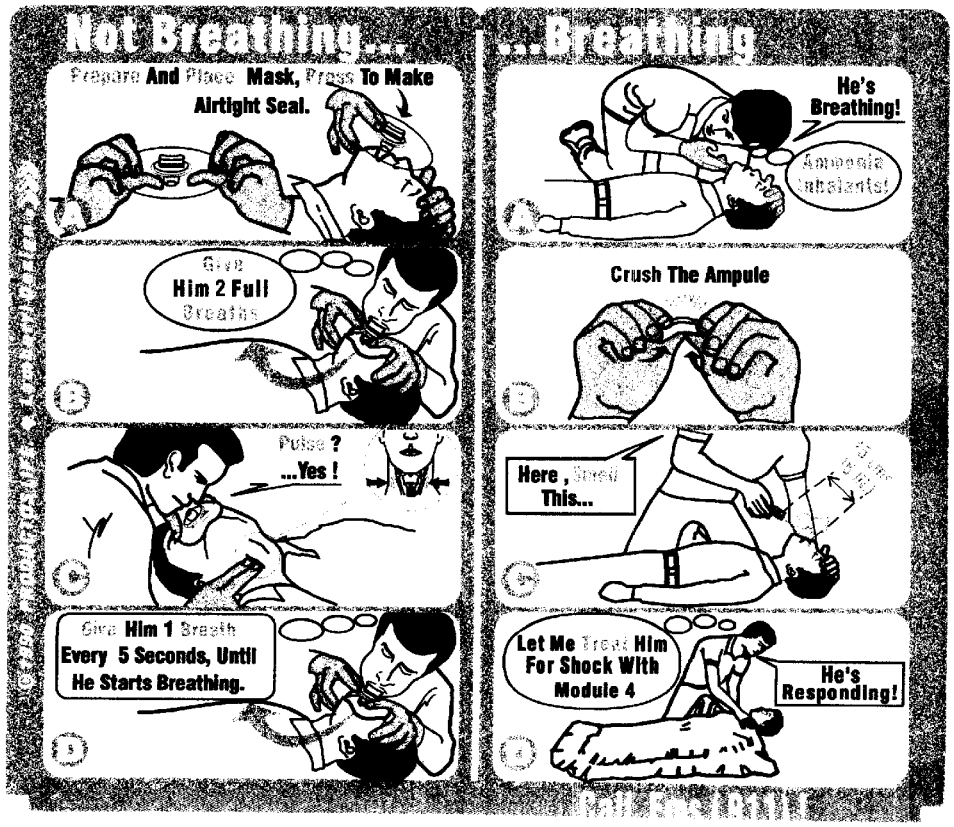
B

Fig. 16
T
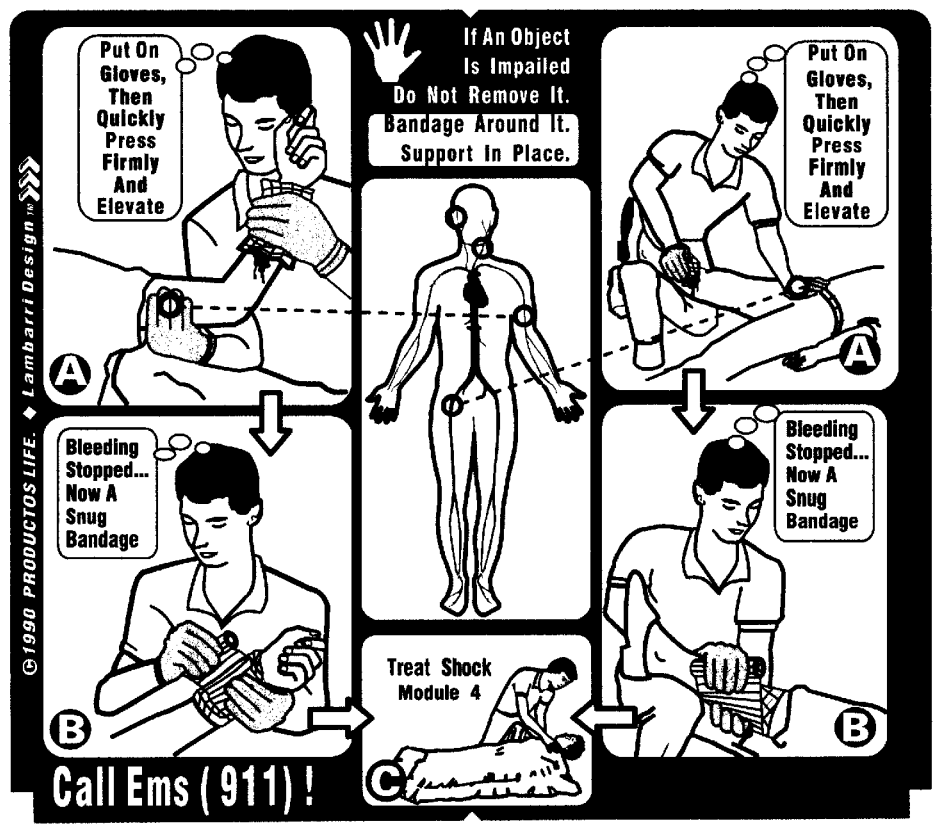
B

T

B

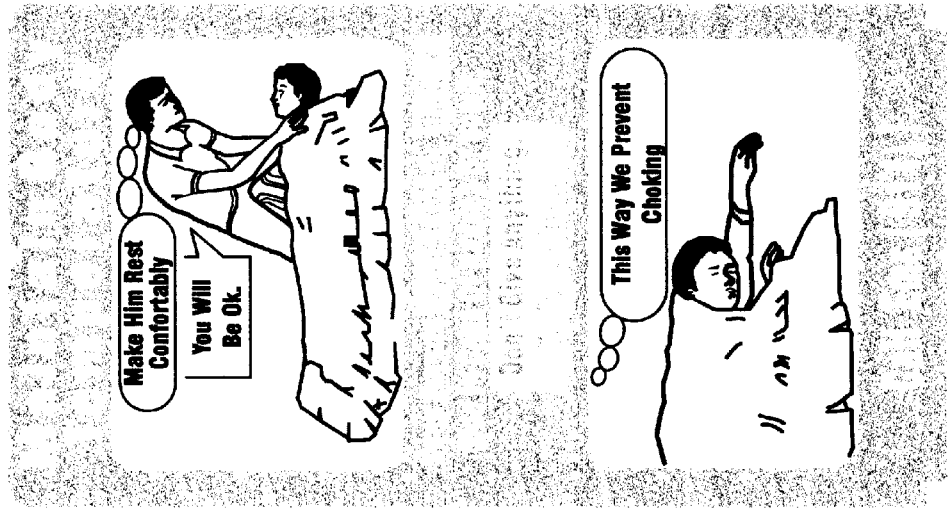
Fig. 18

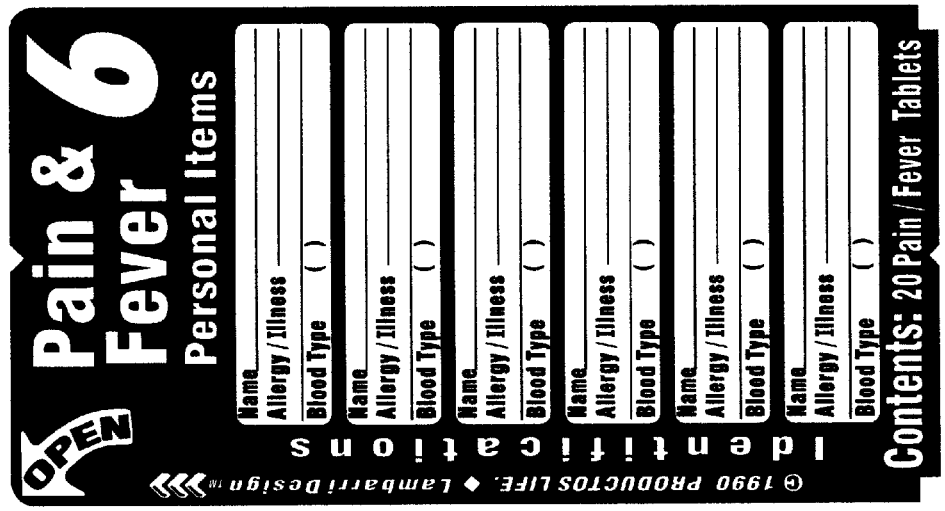
Fig. 20

Fig. 22
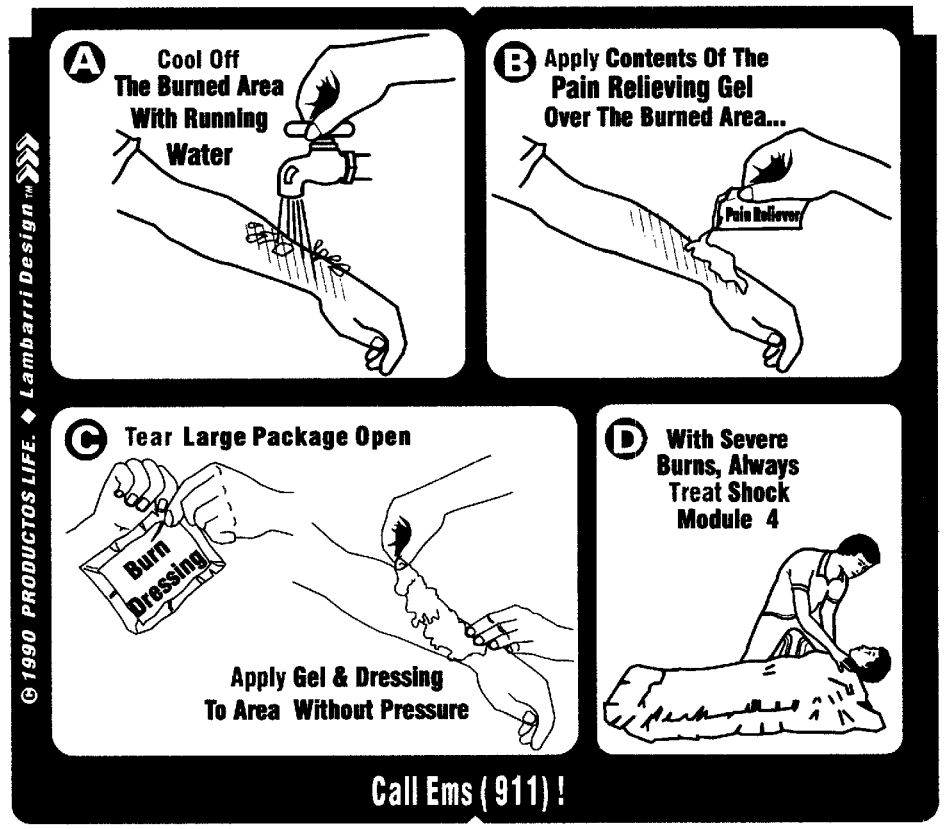
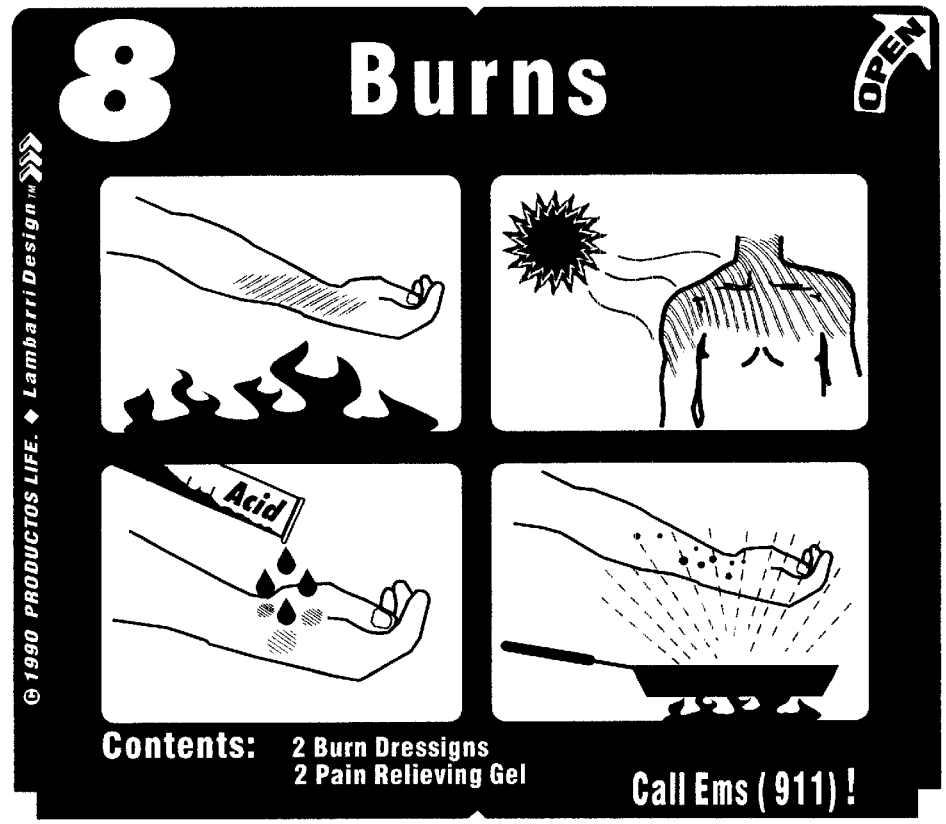

Fig. 23
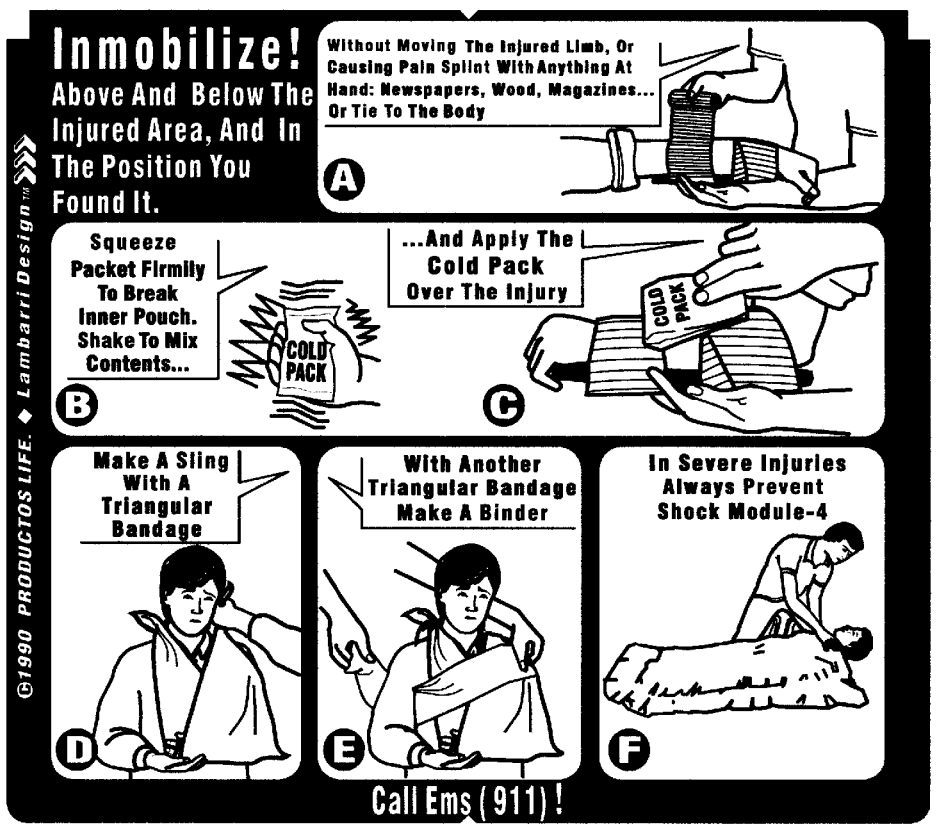

Fig. 24
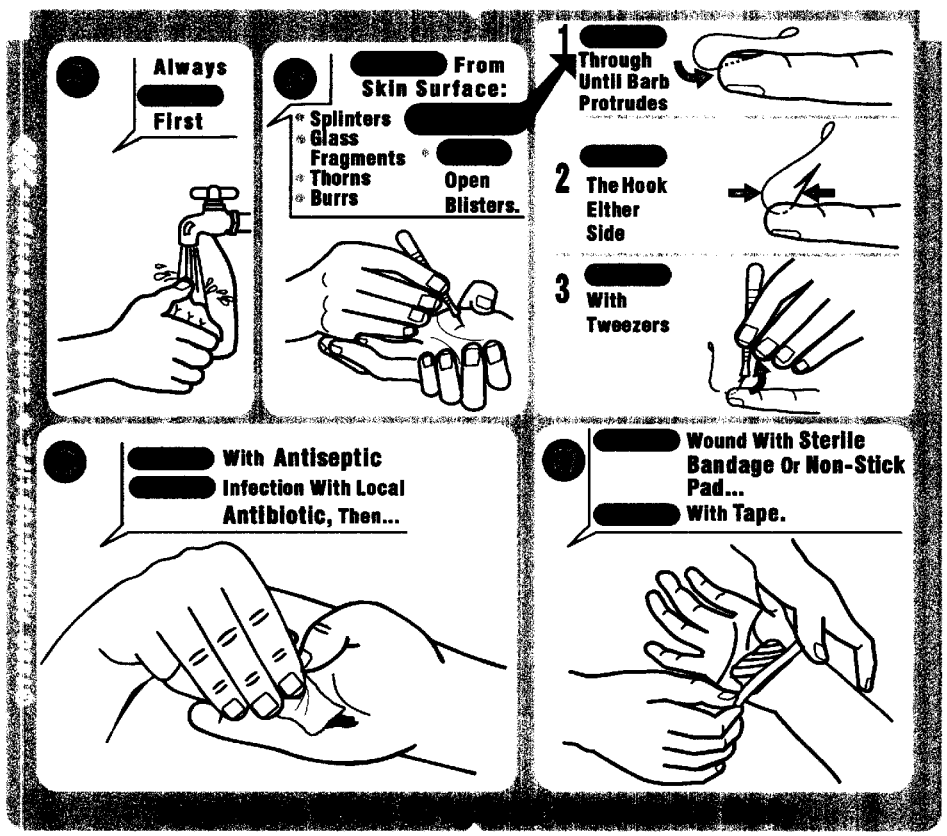
B
T

PRIORITIZED FIRST AID KIT

BACKGROUND OF THE INVENTION

1. Field of the Invention

This invention relates generally to a first aid kit. More specifically, this invention is directed to a modular first aid kit having a plurality of compartments that contain selected articles for treating specific medical emergencies in a prioritized order of life threatening severity.

2. Description of the Related Art

In the field of emergency medical care, a number of first aid kits have been developed for rendering medical care in emergency situations. For example, U.S. Pat. No. 5,848,700 to Horn is directed to an emergency medical care kit having a plurality of compartments containing medical supplies for treating a plurality of medical emergencies. The Horn kit has covers for the compartments which recite the various medical emergencies, and the particular medical emergency recited on each cover is different. However, the various emergencies of the Horn kit are not prioritized, which could lead an unskilled person in a multi-injury situation to proceed in a less than optimal manner, which in turn may result in further injury or even death. Additionally, the Horn kit is made of a pair of organizer units that are inserted into a hard walled carrying case, which appears to be similar to a conventional suitcase. As such, the Horn kit does not appear to be watertight nor to be capable of functioning as a personal flotation device. Further, the installation of the separate organizer units into the carrying case creates an extra step in the manufacturing process. Other currently available first aid kits suffer similar disadvantages.

In light of the foregoing disadvantages, it would be a significant advancement in the art of emergency medical care to provide a buoyant, color-coded, first aid kit that is prioritized with treatments for various medical emergencies in order of life threatening severity to enable an untrained person to render appropriate emergency medical care in time critical situations.

SUMMARY OF THE INVENTION

Accordingly, this invention is directed to an improved first aid kit having a foam case with a plurality of integral, internal compartments containing medical supplies for treating a number of medical emergencies. Each compartment is directed to a specific type of medical emergency, which is identified by indicia on the lid of each compartment. The indicia on the compartment lids preferably contain simple, eye-catching, color-coded graphical illustrations of the particular medical emergencies so that an unskilled person can readily ascertain the appropriate compartments to access in an emergency situation. Additionally, the various medical emergencies are preferably prioritized in order of life threatening severity.

The compartment lids of the present invention are preferably installed with special hinges having ribs that are embedded in the foam of the case to help prevent the hinges from coming loose. Also, a preferred case comprises two interfitting modules that form a watertight seal to a depth of 50 cm. The two modules are connected with hinges that are fastened to the foam with special barbed fasteners. The two modules are also held together with a pair of straps that are fastened to the foam with similar barbed fasteners. A handle is fastened to one of the foam modules with a unique snap-in fastener.

BRIEF DESCRIPTION OF THE DRAWINGS

This invention may best be understood by reference to the following drawings:

FIG. 1A is a side elevational view of a fastener in accordance with the present invention.

FIG. 4 is a sectional view taken along line 4—4 of FIG. 3.

FIG. 5A is an exploded perspective view of an exterior hinge and associated fasteners for the first aid of FIG. 1.

FIG. 5A-1 is a detailed elevational view of an exterior hinge fastener of FIG. 5A.

FIG. 5A-2 is a detailed side elevational view of a portion of the exterior hinge of FIG. 5A.

FIG. 5B is a sectional view showing the installation of an exterior hinge of the first aid kit of FIG. 1.

FIGS. 15–24 are illustrations of preferred indicia on the compartment lids of the first aid kit of FIG. 1.

DETAILED DESCRIPTION OF A PREFERRED EMBODIMENT

Figure 1:
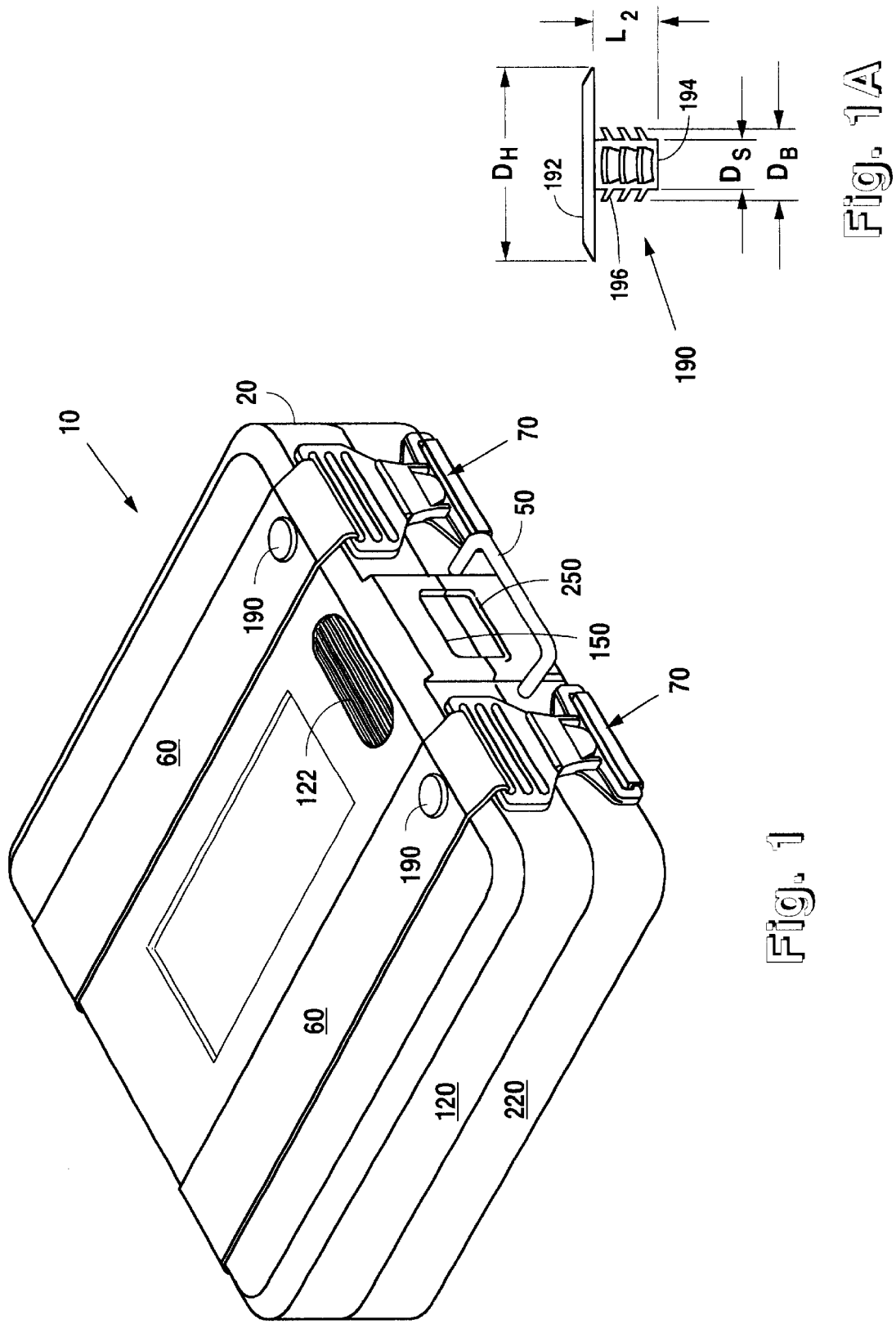
FIG. 1 is a perspective view of a closed first aid kit in accordance with the present invention.
Figure 2:
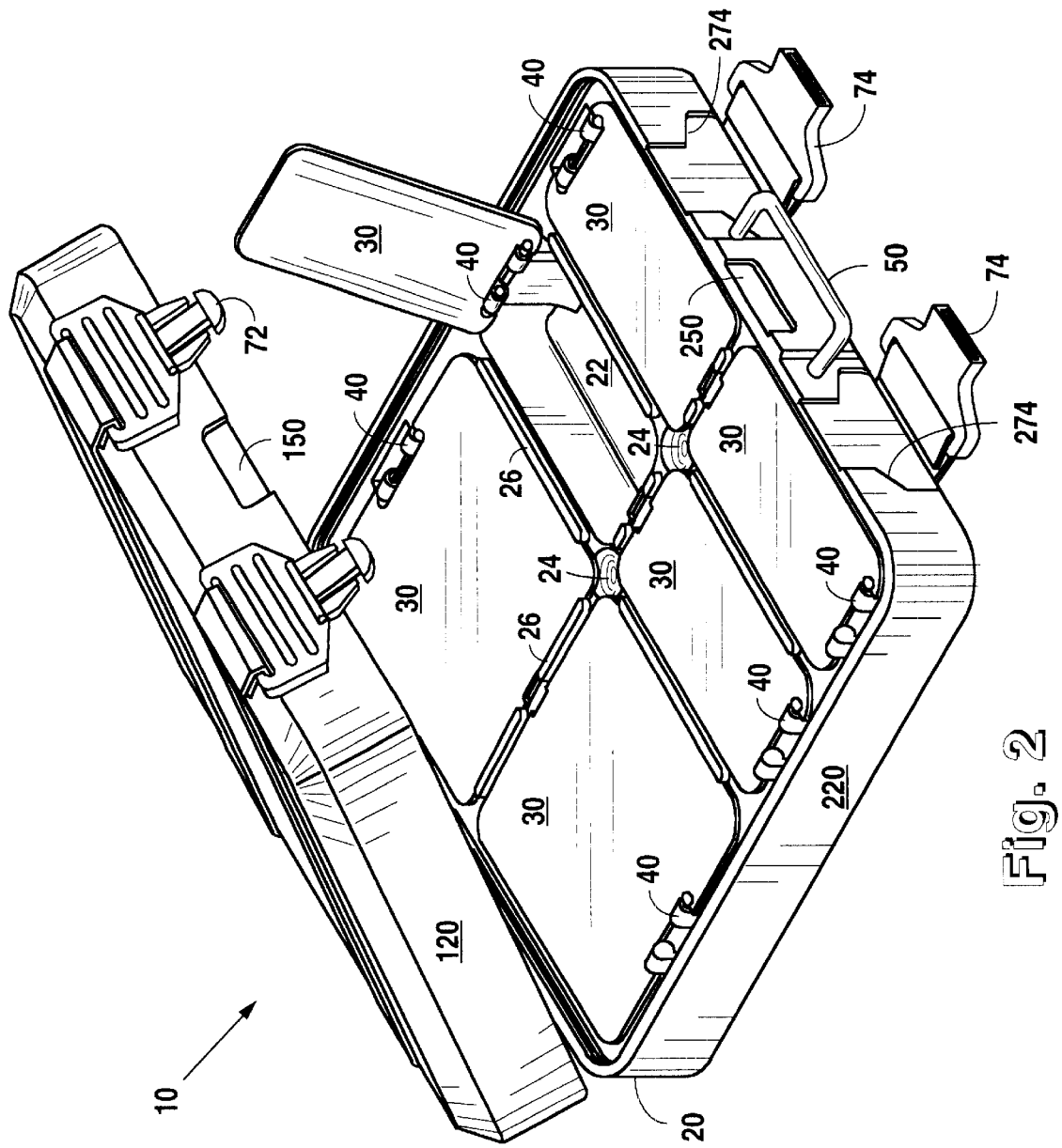
FIG. 2 is a perspective view of the first aid kit of FIG. 1 in a partially opened position.

Referring to FIG. 1, a first aid kit 10 in accordance with the present invention preferably comprises a case 20 having two interfitting modules 120 and 220. Modules 120 and 220 are preferably molded from expanded polypropylene (EPP) foam, which is available from BASF, preferably having a density greater than 60 grams/liter and more preferably having a density of between about 70 grams/liter and 80 grams/liter. The EPP material provides a number of advantages to a first aid kit in accordance with this invention, including resistance to extreme temperatures from −40° C. to 110° C.; resistance to ultraviolet rays; environmental cleanliness due to the absence of CFC agents; light weight; impact and scratch resistance due to a high resilience factor;

and abrasion and chemical resistance due to closed cell construction. However, other forms of foam material, such as polyurethane foam or polyesterene foam, may possibly be used. Modules 120 and 220 are preferably hingedly connected along one edge (see FIGS. 4, 5B, and 8) and fastened together with straps 60 and buckles 70. Straps 60 are preferably made of polypropylene webbing having a thickness of about 1 mm and a width of about 50 mm. Buckles 70 are preferably of the plastic center-release type, each comprising a male buckle 72 and a female buckle 74 (as best shown in FIG. 2) which are fastened to the ends of straps 60 by suitable means, such as stitching. Female buckles 74 preferably lie in matching depressions 274 when buckles 70 are closed. Straps 60 are preferably fastened to modules 120 and 220 with fasteners 190, which are described in more detail below in connection with FIG. 1A. Preferably, an amount of melted silicone is applied to the barbs of fasteners 190 before installation to help secure fasteners 190 in the foam of modules 120 and 220. Additionally, straps 60 are preferably installed in depressions 160 and 260 which are formed about the exterior of modules 120 and 220, respectively, as more clearly shown in FIG. 8. Case 20 preferably has a handle 50, which is described in more detail below in connection with FIGS. 9 and 9A, and depressions 150 and 250 formed in modules 120 and 220, respectively, to assist in opening case 20. Case 20 may also be provided with a gripping area 122 comprising a series of ribs formed in exterior portions of modules 120 and 220 to assist in carrying case 20, which is especially useful if a handle 50 is not provided.

Figure 3:
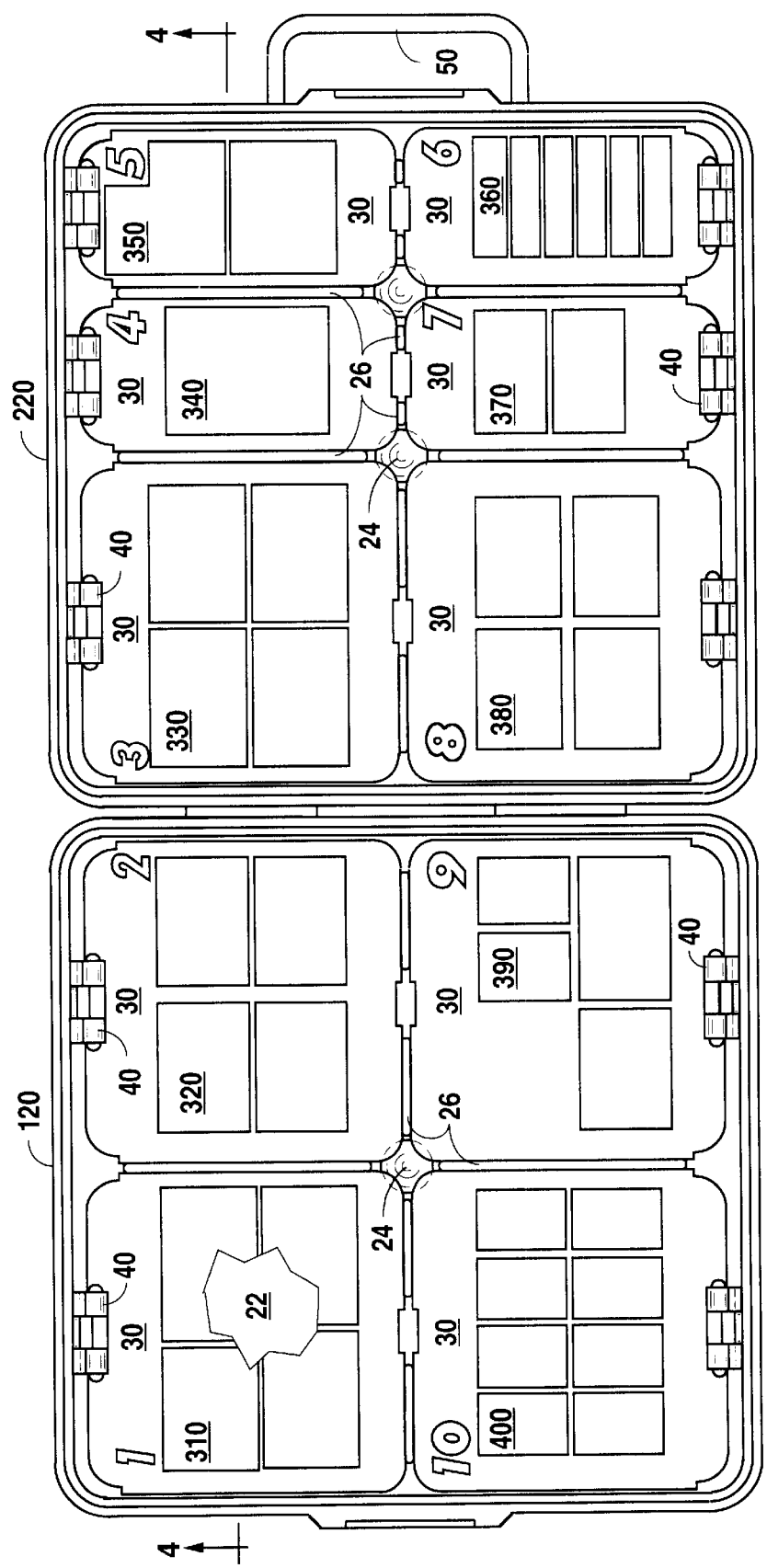
FIG. 3 is a top view of the first aid kit of FIG. 1 in the fully opened position.
Figure 10:
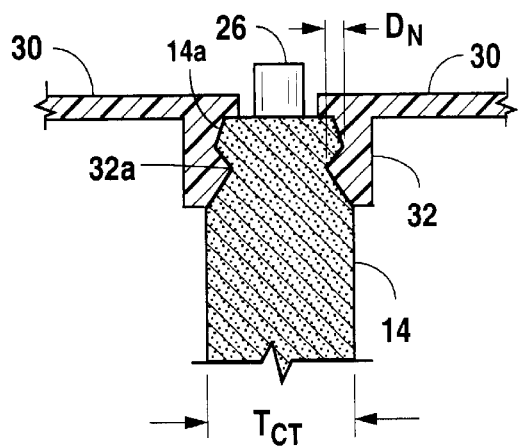
FIG. 10 is a sectional view of two interior compartment lids and a partition of the first aid kit of FIG. 1.
Figure 11A:
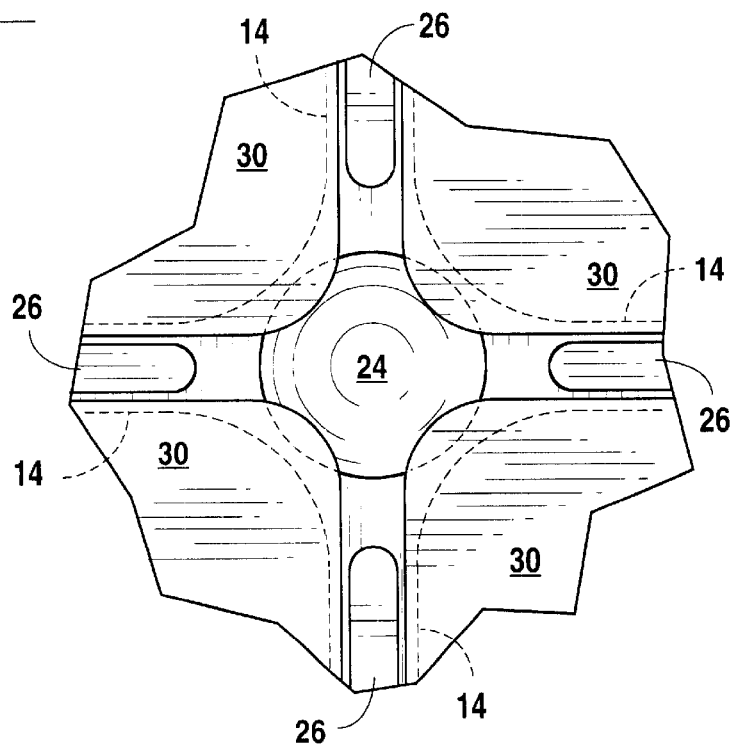
FIG. 11A is a detailed top plan view of a finger depression and adjacent interior compartment lids of the first aid kit of FIG. 1.
Figure 11B:
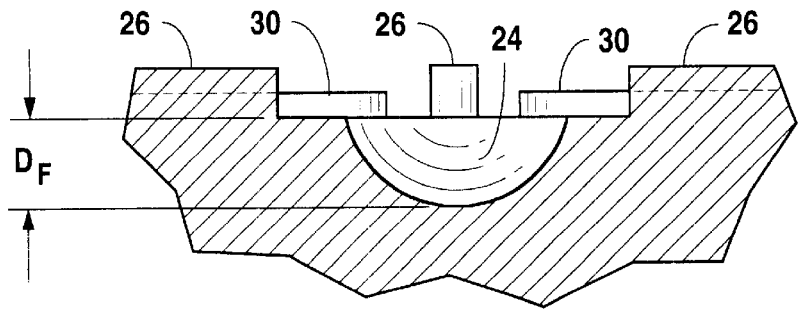
FIG. 11B is a sectional view of the finger depression and adjacent interior compartment lids of FIG. 11A.
Figure 12:
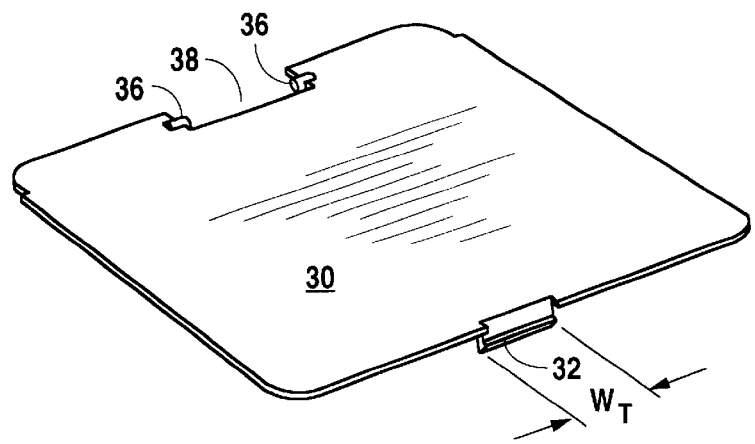
FIG. 12 is a perspective view of an interior compartment lid of the first aid kit of FIG. 1.
Figure 13:
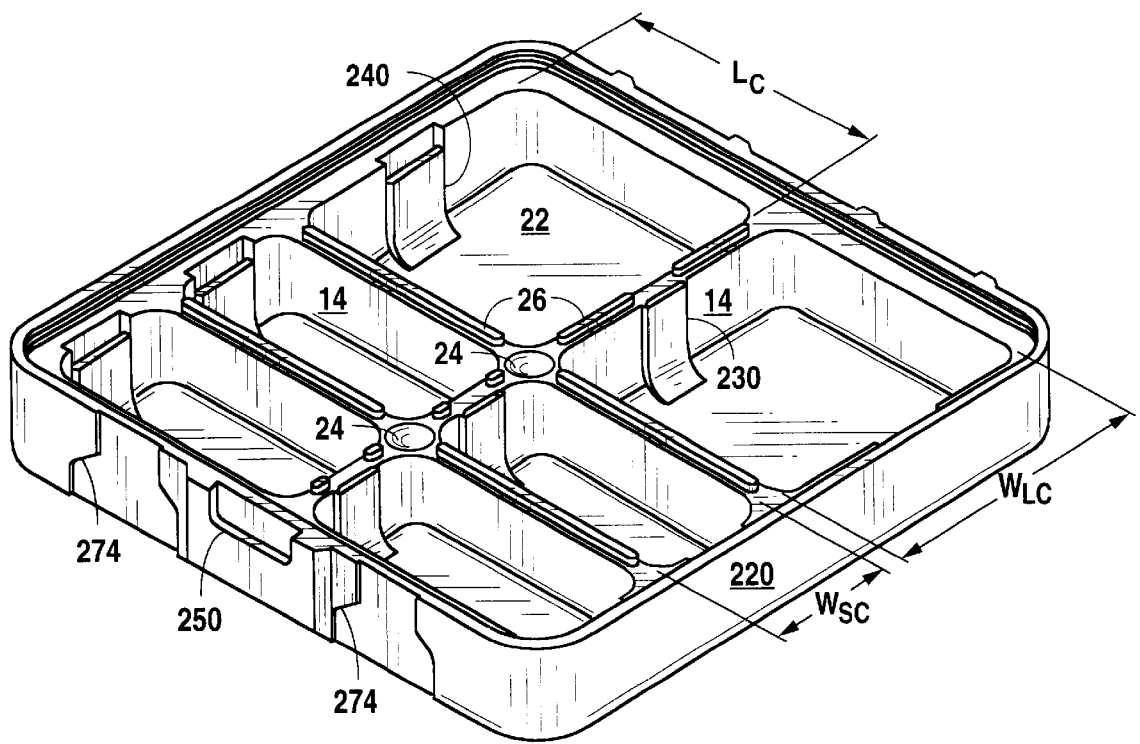
FIG. 13 is a perspective view of one module of the first aid kit of FIG. 1.

As shown in FIGS. 2, 3, and 13, modules 120 and 220 preferably comprise a plurality of compartments 22 integrally formed in the interior of modules 120 and 220 separated by partitions 14. Partitions 14 preferably have a thickness $T_P$ of about 8 mm, as shown in FIG. 4. Compartments 22, which may be of varying sizes, are covered with lids 30 that are installed with hinges 40, preferably along the perimeter of modules 120 and 220. Lids 30 are preferably made of polyestyrene plastic, with a suitable amount of rubber added for flexibility, about 2 mm thick. As illustrated in FIGS. 10 and 12, lids 30 preferably comprise closure tabs 32 having a width $W_T$ of about 20 mm and nibs 32a that engage in corresponding slots formed in partitions 14. Nibs 32a and the corresponding slots in partitions 14 should be of sufficient size to hold lids 30 securely in place. For example, an engagement depth $D_N$ (FIG. 10) of about 1.5 mm is satisfactory under most conditions. Partitions 14 are preferably chamfered as at 14a in FIG. 10 to assist in opening and closing lids 30. As shown in FIG. 13 (in which handle 50 is not shown for clarity), partitions 14 preferably have thickened portions 230 at the locations where closure tabs 32 engage partitions 14. Thickened portions 230 preferably have a thickness $T_{CT}$ of about 11 mm, as shown in FIG. 10. Additionally, finger depressions 24 are preferably formed in modules 120 and 220 at the intersections of partitions 14 to assist in opening lids 30, as detailed in FIGS. 11A and 11B. Finger depressions 24 should be of sufficient size to enable a user to slip a finger underneath the edge of lids 30 for easy opening. For example, a depth $D_F$ (FIG. 11B) of about 8 mm is advantageous.

Figure 8:
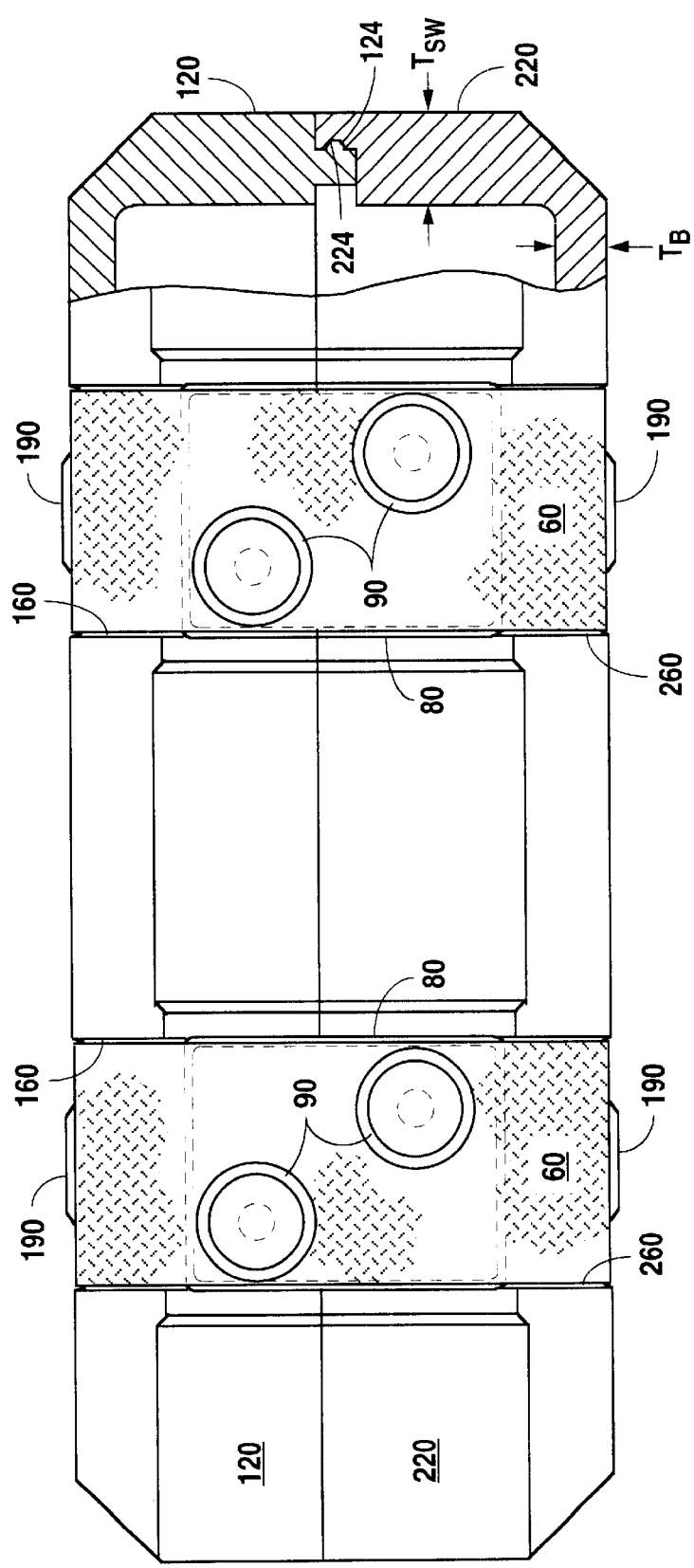
FIG. 8 is a rear elevational, partially sectioned view of the first aid kit of FIG. 1.

As shown in FIG. 8, modules 120 and 220 are preferably connected with a pair of hinges 80, which are installed with fasteners 90. Hinge 80, which is shown in greater detail in FIGS. 5A and 5A-2, is preferably made of polyamide plastic and has holes 82 for receiving fasteners 90. In the vicinity of holes 82, the thickness $T_1$ of hinge 80 is preferably about 2 mm. Hinge 80 preferably narrows in region 86 to a thickness $T_2$ of about 0.43 mm and further narrows in region 88 to a thickness $T_3$ of about 0.33 mm. Surface 84 of hinge 80 mounts against modules 120 and 220, and surface 85 of hinge 80 faces outward. Hinges 80 preferably mount in like-shaped recesses on the exterior of modules 120 and 220. It should be understood that the foregoing dimensions are desirable for purposes of durability but are not limiting for this invention.

As seen in FIGS. 5B and 8, straps 60 preferably overlie hinges 80, and fasteners 90 secure straps 60 and hinges 80 to modules 120 and 220. Referring to FIG. 5A-1, fasteners 90, which are preferably made of polyamide plastic, have a head 92 and a shaft 94 with barbs 96 slanted toward head 92. Head 92 preferably has a diameter $D_H$ of about 13.5 mm. Shaft 94 preferably has a length $L_1$ of about 17 mm and a diameter $D_S$ of about 6.3 mm. The outer diameter $D_B$ of barbs 96 is preferably about 7.5 mm. Preferably, an amount of melted silicone is applied to the barbs of fasteners 90 before installation to help secure fasteners 90 in the foam of modules 120 and 220. Referring to FIG. 5B, at the hinge locations, the wall thickness $T_{CH}$ of modules 120 and 220 is preferably about 22 mm. As shown in FIG. 8, the thickness $T_{SW}$ of the side walls of modules 120 and 220 is preferably about 20 mm, and the thickness $T_B$ of the bottom walls of modules 120 and 220 is preferably about 10 mm (also shown in FIG. 7). Again, it should be understood that the dimensions referenced herein are preferred but are not limiting for this invention.

As shown in FIG. 1A, fasteners 190 are similar to fasteners 90, except that fasteners 190 are shorter and have a blunt tip for use with relatively thin foam material. Specifically, fasteners 190, which are also preferably made of polyamide plastic, have a head 192 and a shaft 194 with barbs 196 slanted toward head 192. Dimensions $D_H$, $D_S$, and $D_B$ are preferably the same as discussed above for fasteners 90, and length $L_2$ is preferably about 9 mm.

Referring to FIGS. 4, 5B, and 8, module 120 preferably has an integral protrusion 124 around its perimeter that mates with recess 224 on module 220 to create a watertight seal when case 20 is closed. The watertight seal is effective to a depth of about 50 cm when kit 10 is submersed in water. To enhance such seal, protrusion 124 is preferably slightly larger than recess 224. A preferred nominal radius for protrusion 124 and recess 224 is about 1.5 mm. Alternatively, an O-ring could be used.

Referring to FIGS. 2, 3 and 13, partitions 14 of modules 120 and 220 preferably have a plurality of ribs 26 such that, when case 20 is closed, the ribs 26 of module 120 align with and butt up against the ribs 26 of module 220 to provide lateral support and help prevent collapse of case 20. Ribs 26 also serve to hold lids 30 in place.

Figure 6:
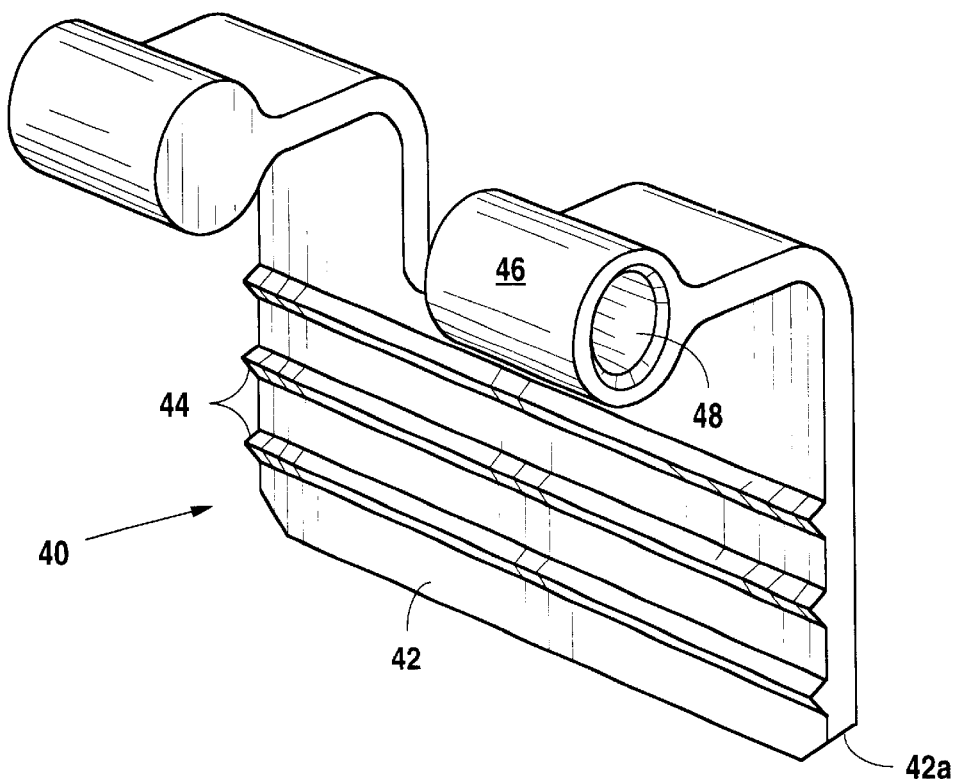
FIG. 6 is a perspective view of an interior compartment lid hinge of the first aid kit of FIG. 1.

FIG. 6 shows a preferred lid hinge 40 for installing lids 30. Hinge 40 is preferably made of polyacetal plastic and has a generally planar tab 42 for insertion into corresponding slots in modules 120 and 220, with chamfers 42a for assisting such insertion. Tab 42 of hinge 40 preferably has at least one rib 44 extending laterally from tab 42 to help secure tab 42 within the corresponding slots in modules 120 and 220. Hinge 40 has a pair of cylindrical bosses 46, each of which has an outwardly facing cylindrical recess 48. As shown in FIG. 12, lid 30 has a pair of cylindrical hinge pins 36 which face each other on either side of slot 38. Lid 30 is installed by squeezing bosses 46 of hinge 40 toward one another sufficiently to allow insertion of hinge pins 36 into recesses 48. Alternatively, the hinge pins may be on lid hinge 40 and the cylindrical recesses may be on lid 30.

Figure 7:
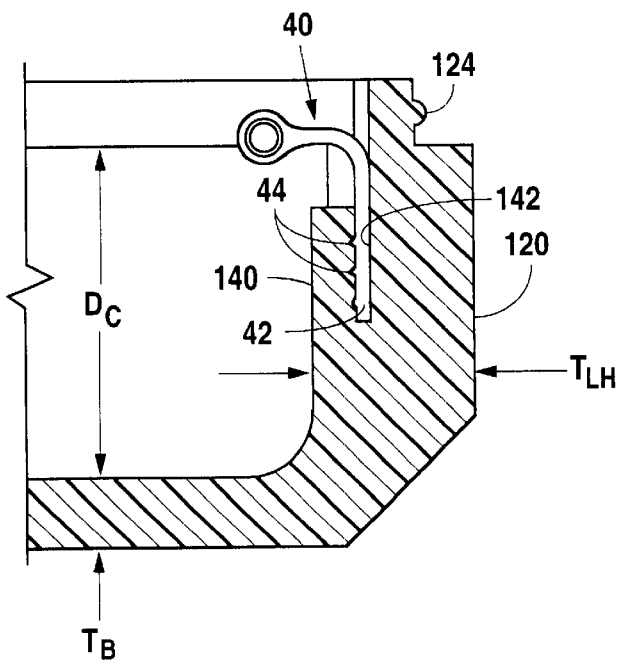
FIG. 7 is a sectional view showing the installation of an interior compartment lid hinge of the said kit of FIG. 1.

Referring to FIGS. 4 and 13, the side walls of modules 120 and 220 are preferably provided with thickened areas 140 and 240, respectively, at the locations where lid hinges 40 are installed. For example, a thickness $T_{LH}$ of about 23 mm is preferred. As shown in FIG. 7, thickened area 140 has a rectangular slot 142 for receiving tab 42 of lid hinge 40. Slot 142 is preferably slightly undersized with respect to tab 42 such that tab 42 must be forced into slot 142. Ribs 44 also help to secure tab 42 of hinge 40 in slot 142, and melted silicone or a suitable adhesive may also be used to further secure hinge 40 in place. Hinges 40 are similarly installed in modules 120 and 220. It should be noted that hinges 40 are preferably installed about the perimeter of modules 120 and 220 such that lids 30 open outward to avoid concealing an adjacent compartment when a lid 30 is opened. In this manner, all compartments 22 may be accessed simultaneously, if desired.

Turning now to FIG. 3, each compartment 22 is preferably dedicated to hold medical supplies for a particular type of medical emergency as identified by indicia 310–400 on the top of each lid 30. Indicia 310–400 preferably comprise simple but eye-catching graphics that enable an unskilled person quickly to ascertain the purpose of the medical supplies within each compartment 22. More preferably, indicia 310–400 are also color-coded, the graphics on each lid 30 being a different color. Even more preferably, the various medical emergencies that the contents of each compartment 22 are used to treat are prioritized in order of life threatening severity, and lids 30 are numbered accordingly. Likewise, the bottom side of each lid 30 preferably bears instructions regarding the proper use of the contents of that particular compartment 22 to treat the particular medical emergency. FIGS. 15 through 24 are examples of preferred indicia for the tops (indicated by the letter "T" for "top") and bottoms (indicated by the letter "B" for "bottom") of lids 30.

Figure 9:
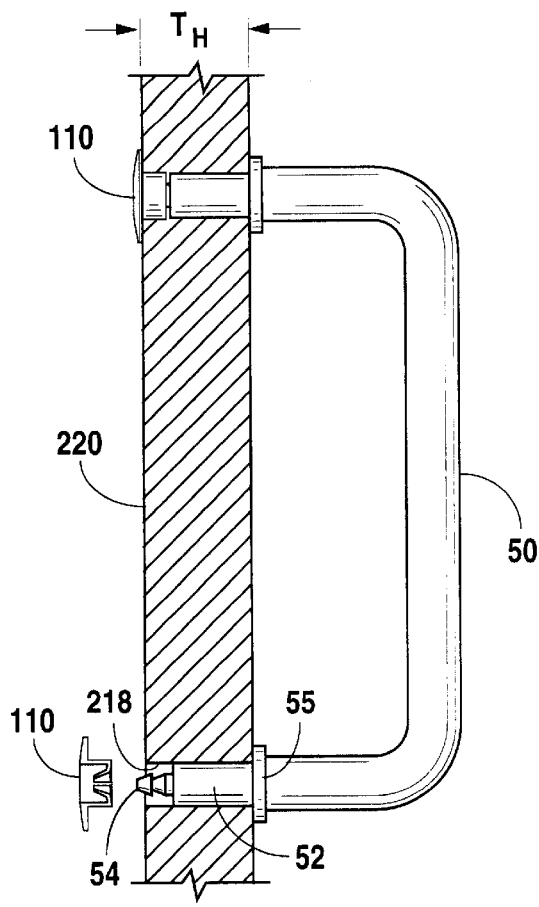
FIG. 9 is partially sectioned, partially exploded view showing the installation of the handle of the first aid kit of FIG. 1.
Figure 9B:
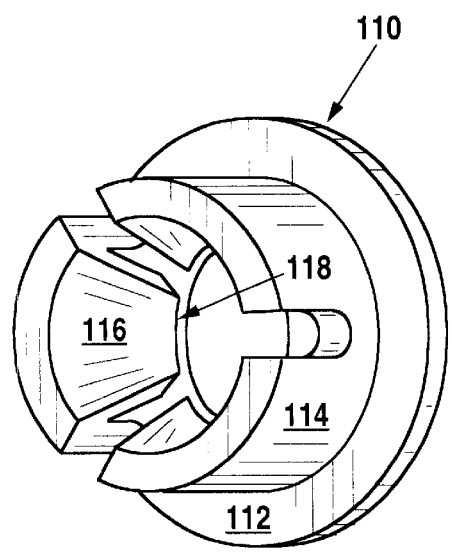
FIG. 9B is a perspective view of a snap-in fastener of FIG. 9.
Figure 9A:
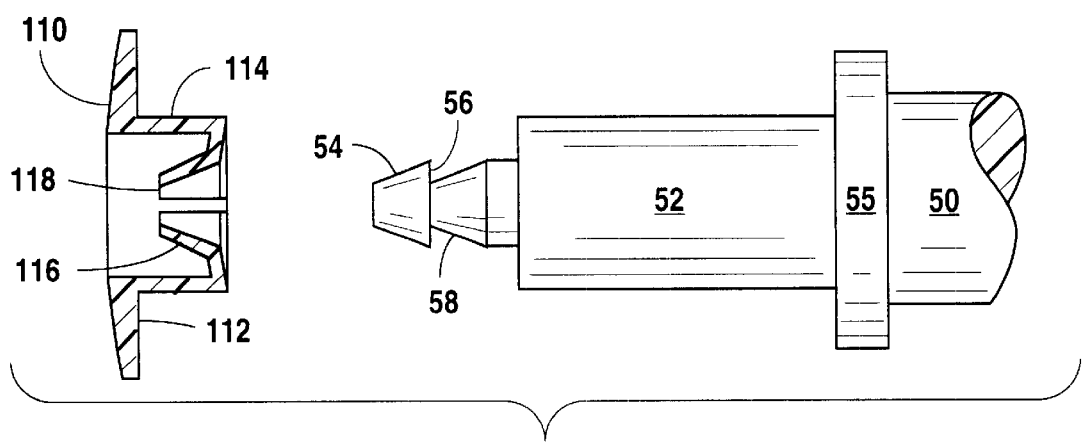
FIG. 9A is an exploded, partially sectioned view of a portion of FIG. 9.

As illustrated in FIGS. 9, 9A, and 9B, handle 50 is preferably fastened to module 220 of case 20 by means of unique snap-in fasteners 110 in cooperation with special probes 54 on handle 50. Each leg of handle 50, which is preferably made of polyamide plastic, has a collar 55, a stem 52, and a truncated conical probe 54 extending from a conical support section 58. Fastener 110, which is also preferably made of polyamide plastic, has a cylinder 114 extending from a base 112. At the end of cylinder 114 opposite base 112, fastener 110 has a set of prongs 116 extending into the interior of cylinder 114. Prongs 116 extend from cylinder 114 in a conical arrangement to match probe 54 of handle 50. Although any desired number of prongs 116 may be employed, a set of three prongs 116 of roughly equal arclength is preferred. Thickness $T_H$ of the wall of module 220 is preferably about 20 mm in the vicinity of handle 50. To install handle 50, stem 52 is inserted into a hole 218 from the exterior of a wall of module 220 until collar 55 is flush with module 220. Then, as fastener 110 is pressed into hole 218 from the interior side of the wall of module 220, probe 54 of handle 50 engages prongs 116 of fastener 110. As fastener 110 is pressed onto probe 54, prongs 116 flex outward until catch 56 of probe 54 moves past tips 118 of prongs 116. At that point, prongs 116 snap back to their initial position and engage conical support section 58, and catch 56 holds fastener 110 in place. To allow such installation, fastener 110 and stem 52 are sized such that a slight gap, preferably about 1 mm, exists between the end of fastener 110 and stem 52 in the installed position.

Figure 14:
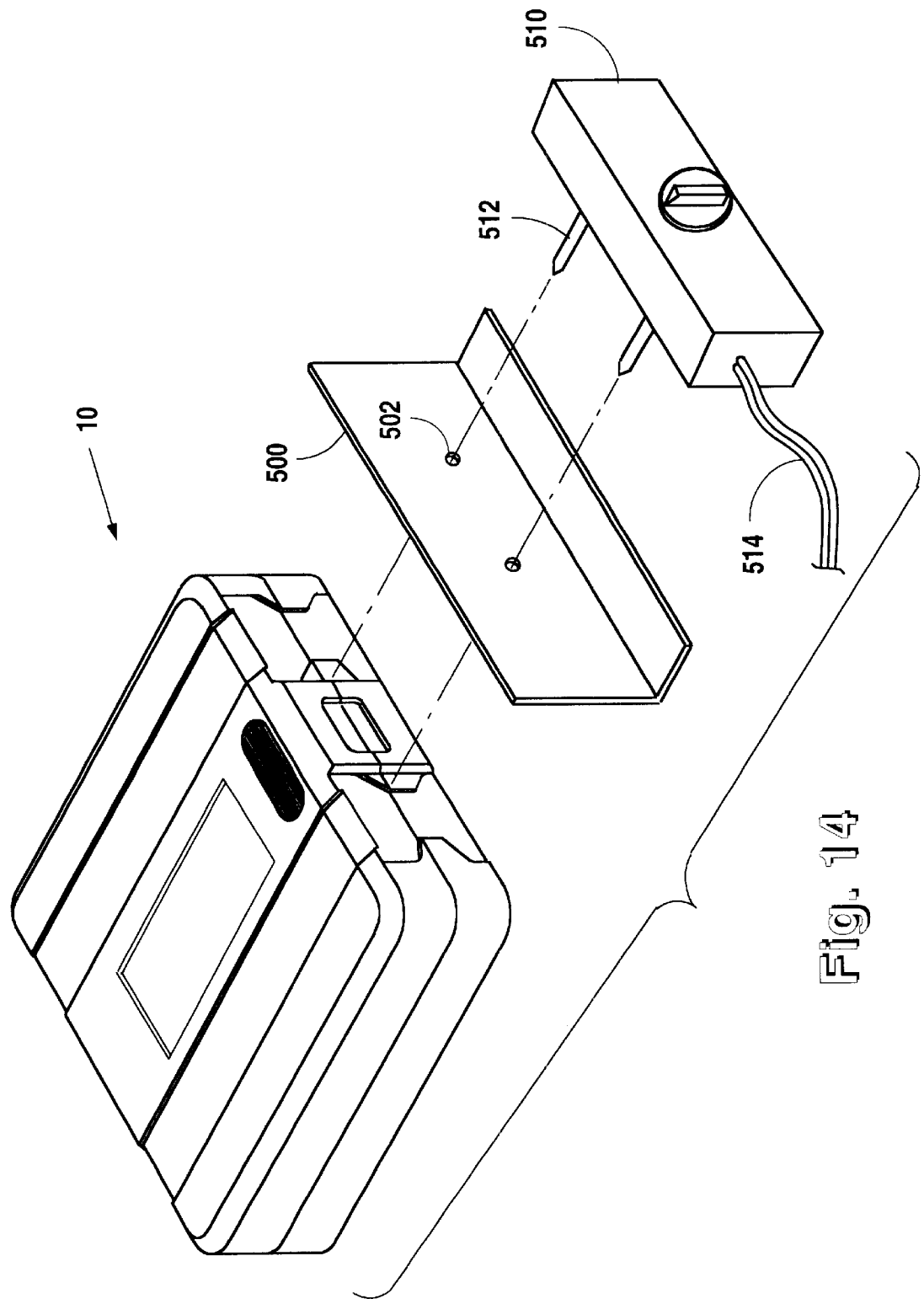
FIG. 14 is an exploded perspective view illustrating a method of making holes for installation of fasteners on the first aid kit of FIG. 1.
Figure 17:
Figure 19:
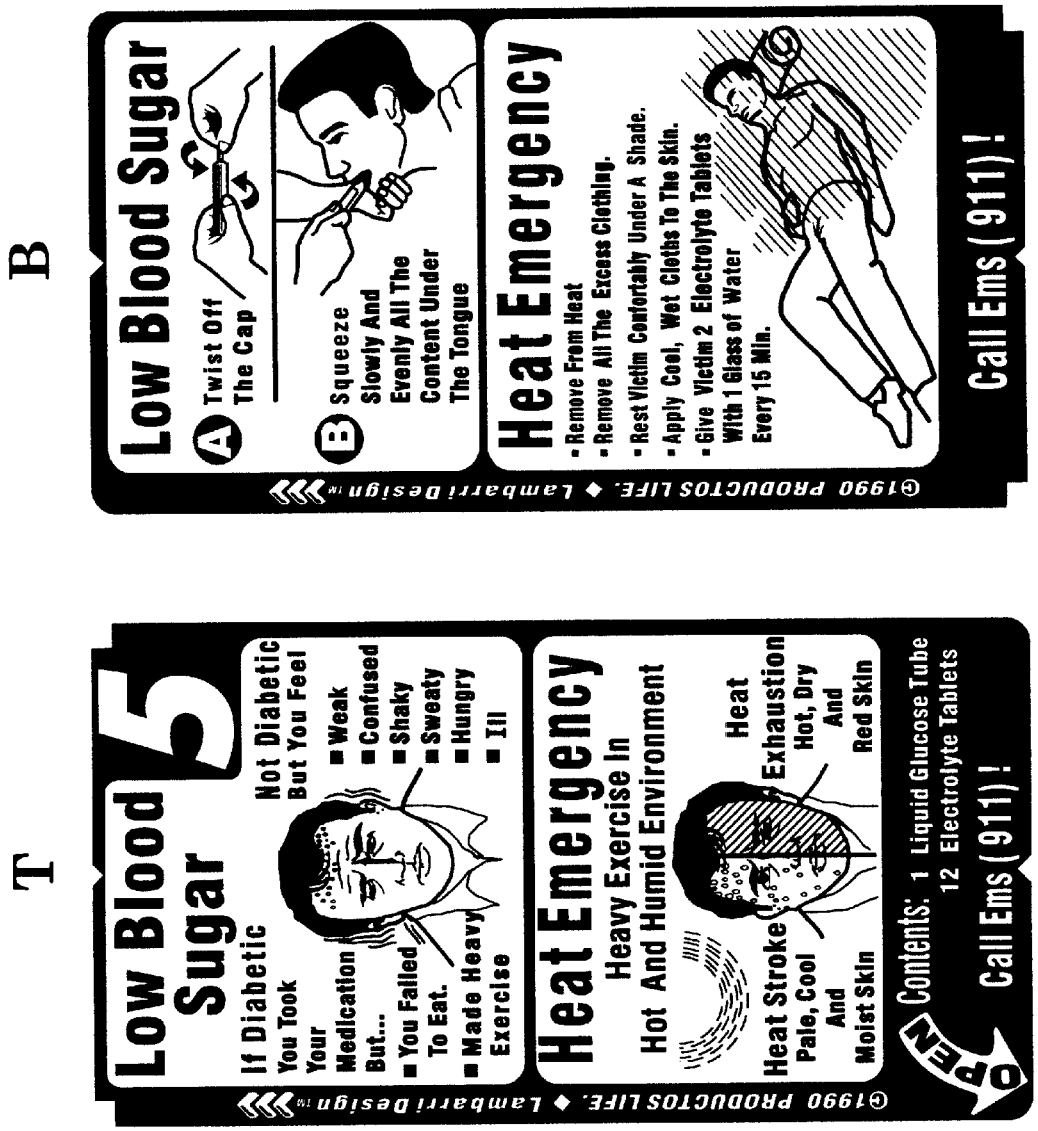
Figure 21:
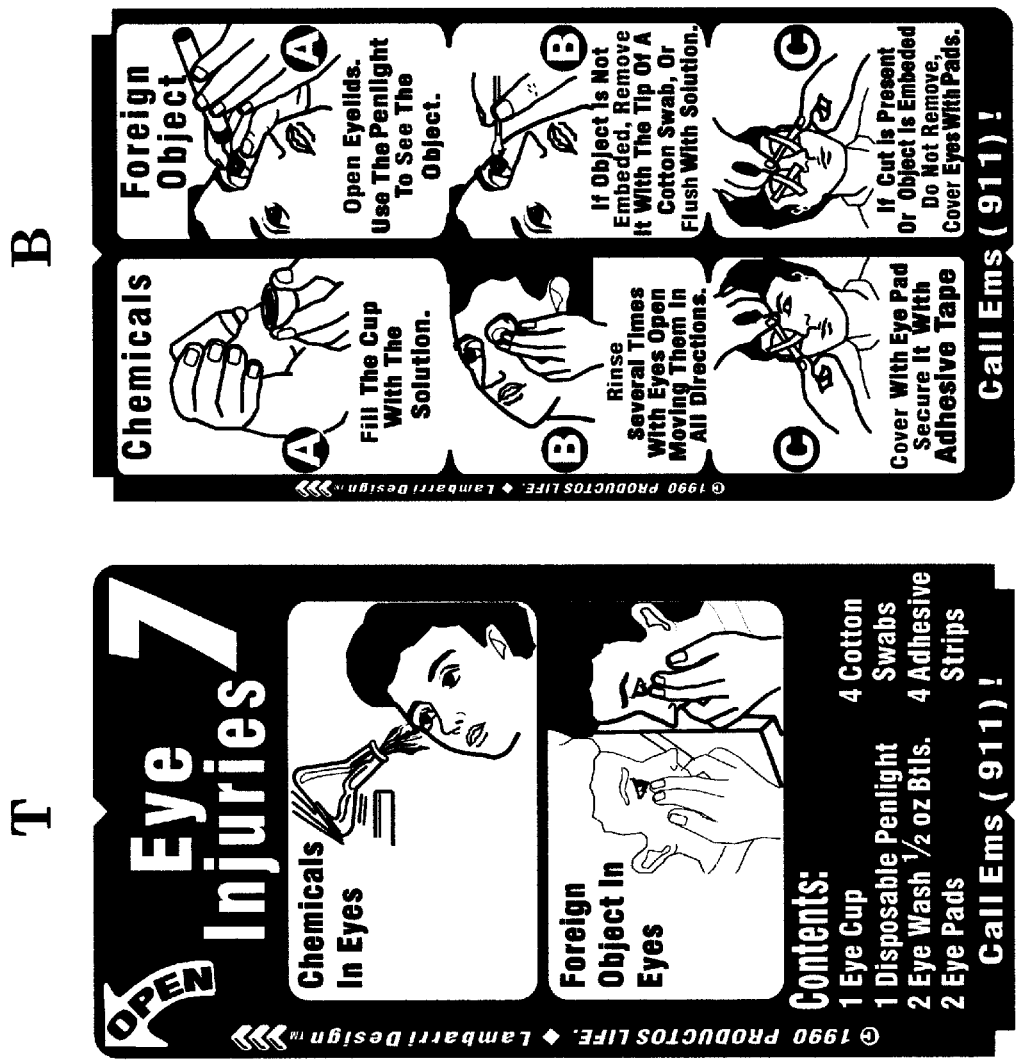

FIG. 14 illustrates a preferred method of making the holes in kit 10 necessary to install handle 50. Kit 10 is preferably immobilized in a jig (not shown), and a template 500 having predrilled holes 502 at the desired fastener locations is placed adjacent kit 10. A tool 510 having a set of rods 512 is used to make the necessary holes by heating rods 512, preferably by an electrical connection 514 to a source of electricity (not shown); aligning rods 512 with predrilled holes 502; and inserting heated rods 512 through holes 502 and the foam wall of kit 10. For a kit 10 made of EPP, rods 512 should be heated to between about 120° C. and about 130° C. Recesses for installing barbed fasteners 90 and 190 may be made in like manner, except that heated rods 512 are inserted into the foam of kit 10 only to a predetermined depth rather than completely through the foam.

It will be appreciated that barbed fasteners 90 and 190 and snap-in fastener 110 may be used to fasten any of a variety of items to a foam product. Such items may include handles, hinges, knobs, straps, placards, and the like, or even other foam products. Any such item to be fastened to a foam product is referred to herein as an accessory.

One of the attractive features of first aid kit 10 is that its mass and volume combination make it buoyant in water, even when compartments 22 are filled with a preferred set of medical supplies, which are listed in Table 1. By way of example, a preferred embodiment as described herein has exterior dimensions of about 335 mm×328 mm×118 mm for an overall volume of about 13,000 cm$^3$ and an empty mass of about 870 grams. As shown in FIGS. 4, 7, and 13, compartments 22 preferably have a length $L_C$ of about 140 mm and a depth $D_C$ of about 45 mm. The large compartments preferably have a width $W_{LC}$ of about 140 mm, and the small compartments preferably have a width $W_{SC}$ of about 66 mm. With a total mass of about 2000 grams when full of medical supplies, the overall density is about 0.15 grams/cm$^3$, which is less than that of water (1.0 gram/cm$^3$), thereby making kit 10 buoyant in water. Furthermore, the buoyancy of kit 10 is sufficient to float a mass of 5 kg in water. As the average mass of a human head is about 5 kg, kit 10 is capable of being used as a personal flotation device to help a person keep his or her head above water and thereby avoid drowning. Persons reasonably skilled in the art will appreciate that the dimensions, materials, and contents of kit 10 may be varied as necessary to achieve a desired level of buoyancy.

Although the foregoing specific details describe a preferred embodiment of this invention, persons reasonably skilled in the art will recognize that various changes may be made in the details of the apparatus of this invention without departing from the spirit and scope of the invention as defined in the appended claims. Therefore, it should be understood that this invention is not to be limited to the specific details shown and described herein.

TABLE 1

Preferred Contents

| Seq. No | Item Description | Qty. per kit |
|---|---|---|
| 1 | Activated Charcoal | 1 oz. bottle |
| 2 | Adhesive Tape ½" × 5 yd waterproof | 1 roll |
| 3 | Ammonia inhalants | 3 ampules |
| 4 | Burn-Jel 3.5 gr-⅛ oz. from Water Jel (pain relieving gel) | 2 foils |
| 5 | Butterfly adhesive closures | 5 individual |
| 6 | BZK Antiseptic towelettes | 13 foiled pkgs. |
| 7 | Cetafen non-aspirin (acetaminophen pkts of 2 ea.) | 10 foils w/2 ea. |
| 8 | Cold pack (small) in unit box | 2 individual pkgs. |
| 9 | Cotton tip applicator 3" (eye swabs) | 4 swabs |
| 10 | CPR Micromask kit (collapsible mask, pair latex gloves, 1-way valve) | 1 nyon pouch |
| 11 | Elastic bandage 3" Roll | 1 individual wrap |
| 12 | Elastic patch large cloth bandage 2 × 3 in | 4 individual |
| 13 | Electrotab Electrolyte tablets (2 per packet) | 6 foils w/2 ea. |
| 14 | Eye cups, non sterile, plastic. | 1 individual |
| 15 | Eye Pads, dressings (4 w/adhesive tape strips in unit packet) | 1 individual box |
| 16 | Eyewash 1/2 oz., sterile | 2 bottles |
| 17 | Fingertip Bandage 1¾" × 2" | 3 individual |
| 18 | Forceps first aid kit type tweezers 4" | 1 individual |
| 19 | Gloves, non-sterile latex (1 pair in bag) | 1 pair (medium size) |
| 20 | Insect sting relief medicated pads | 3 foil pkgs. |
| 21 | Insta-Glucose for insulin reactions (Dextrose 43%, liquid) | 1 individual tube |
| 22 | Ipecac (Syrup, 1 oz. bottle) | 1 bottle |
| 23 | Knuckle Bandage (medium size) | 3 individual |
| 24 | Non-adherent pads 2 × 3 in | 10 individuals |
| 25 | Penlight with pupil gauge (disposable) | 1 individual |
| 26 | Plastic strips 1 × 3 in (band-aids) | 20 individual |
| 27 | Pressure Pad Compress 5 × 6 in (extra absorbent pad + rollerbandage) | 1 blood stopper |
| 28 | Rescue Blanket unit box (thermal blanket 56" × 84") | 1 individual |
| 29 | Scissors 4" First aid type w/blunt ends | 1 individual |
| 30 | Triangle Bandages Muslin 40 × 40 × 56 in. | 2 in poly bag individual |
| 31 | Triple Antibiotic ointment (foil packets) | 10 individual pkgs. |
| 32 | Venom Extractor + (4 cups, different sizes, razor & tourniquet) | 1 kit |
| 33 | Water Jel burn dressing 2" × 6" (sterile) | 2 foils |

I claim:

1. A first aid kit, comprising:

a case comprised of EPP foam having a density greater than 60 grams/liter, said case having a plurality of compartments and comprising a first case module and a second case module, said first case module comprising a peripheral protrusion having a semicircular cross-sectional shape, said second case module comprising a peripheral recess having a semicircular cross-sectional shape, wherein said peripheral protrusion mates with said peripheral recess to form a watertight seal;

a plurality of lids respectively covering said plurality of compartments wherein each of said plurality of lids identifies a particular medical emergency, the particular medical emergency on each of said plurality of lids being different and being prioritized according to severity by ordered positional placement within said case; and medical supplies selectively contained within each of said plurality of compartments for treating the particular medical emergency respectively identified on each of said plurality of lids.

2. The first aid kit of claim 1 wherein each of said plurality of lids has a bottom side bearing instructions concerning the use of said medical supplies for treating the particular medical emergency respectively identified on each of said plurality of lids.

3. A first aid kit, comprising:

a case comprised of EPP foam having a density greater than 60 grams/liter, said case having a plurality of compartments and comprising a first case module and a second case module, said first case module comprising a peripheral protrusion having a semicircular cross-sectional shape, said second case module comprising a peripheral recess having a semicircular cross-sectional shape, wherein said peripheral protrusion mates with said peripheral recess to form a watertight seal;

a plurality of lids respectively covering said plurality of compartments wherein each of said plurality of lids bears a graphical illustration of a particular medical emergency, the particular medical emergency on each of said plurality of lids being different; and medical supplies selectively contained within each of said plurality of compartments for treating the particular medical emergency respectively illustrated on each of said plurality of lids.

4. The first aid kit of claim 3 wherein each of said plurality of lids has a bottom side bearing instructions concerning the use of said medical supplies for treating the particular medical emergency respectively illustrated on each of said plurality of lids.

5. A first aid kit, comprising:

a case comprised of EPP foam having a density greater than 60 grams/liter, said case having a plurality of compartments and comprising a first case module and a second case module, said first case module comprising a peripheral protrusion having a semicircular cross-sectional shape, said second case module comprising a peripheral recess having a semicircular cross-sectional shape, wherein said peripheral protrusion mates with said peripheral recess to form a watertight seal, each of said plurality of compartments having a slot for receiving a lid hinge;

a plurality of lid hinges, each of said hinges having a generally planar tab with at least one rib thereon and a pair of bosses extending from said tab, each of said bosses having a generally cylindrical recess, said at least one rib on said tab of each of said lid hinges being disposed within said slot of each respective compartment;

a plurality of lids respectively covering said plurality of compartments wherein each of said plurality of lids identifies a particular medical emergency, the particular medical emergency on each of said plurality of lids being different, each of said plurality of lids having a pair of generally cylindrical hinge pins respectively disposed within said recesses of said pair of bosses of each respective lid hinge; and medical supplies selectively contained within each of said plurality of compartments for treating the particular medical emergency respectively identified on each of said plurality of lids.

6. The first aid kit of claim 5 wherein each of said plurality of lids has a bottom side bearing instructions concerning the use of said medical supplies for treating the particular medical emergency respectively identified on each of said plurality of lids.

7. A first aid kit, comprising:

a case comprised of EPP foam having a density greater than 60 grams/liter, said case having a plurality of compartments and comprising a first case module and a second case module, said first case module comprising a peripheral protrusion having a semicircular cross-sectional shape, said second case module comprising a peripheral recess having a semicircular cross-sectional shape, wherein said peripheral protrusion mates with said peripheral recess to form a watertight seal, each of said plurality of compartments having a slot for receiving a lid hinge;

a plurality of lid hinges, each of said plurality of lid hinges having a generally planar tab with at least one rib thereon and a pair of generally cylindrical hinge pins extending from said tab, said at least one rib on said tab of each of said plurality of lid hinges being disposed within said slot of each respective compartment;

a plurality of lids respectively covering said plurality of compartments wherein each of said plurality of lids identifies a particular medical emergency, the particular medical emergency on each of said plurality of lids being different, each of said plurality of lids having a pair of bosses with a respective pair of generally cylindrical recesses, wherein said pair of hinge pins is respectively disposed within said recesses of said pair of bosses of each respective lid hinge; and medical supplies selectively contained within each of said plurality of compartments for treating the particular medical emergency respectively identified on each of said plurality of lids.

8. The first aid kit of claim 7 wherein each of said plurality of lids has a bottom side bearing instructions concerning the use of said medical supplies for treating the particular medical emergency respectively identified on each of said plurality of lids.

9. A first aid kit, comprising:

a first case module comprised of EPP foam having a density greater than 60 grams/liter, said first case module having at least one compartment and a peripheral protrusion having a semicircular cross-sectional shape;

a second case module comprised of EPP foam having a density greater than 60 grams/liter, said second case module having at least one compartment and a peripheral recess having a semicircular cross-sectional shape, wherein said peripheral protrusion mates with said peripheral recess to form a watertight seal;

a plurality of lids respectively covering said at least one compartment of said first and second case modules wherein each of said plurality of lids identifies a particular medical emergency, the particular medical emergency on each of said plurality of lids being different and being prioritized according to severity by ordered positional placement within said first and second case modules; and medical supplies selectively contained within said at least one compartment of said first and second case modules for treating the particular medical emergency respectively identified on each of said plurality of lids.

10. The first aid kit of claim 9 wherein each of said plurality of lids has a bottom side bearing instructions concerning the use of said medical supplies for treating the particular medical emergency respectively identified on each of said plurality of lids.

11. The first aid kit of claim 9 wherein each of said plurality of lids bears a graphical illustration of the particular medical emergency respectively identified on each of said plurality of lids.

12. The first aid kit of claim 9 further comprising:

a plurality of lid hinges, each of said plurality of lid hinges having a generally planar tab with at least one rib thereon and a pair of bosses extending from said tab, each of said bosses having a generally cylindrical recess;

wherein said at least one compartment of said first and second case modules has a slot for receiving a lid hinge, said at least one rib on said tab of each of said plurality of lid hinges being respectively disposed within said slot of said at least one compartment of said first and second case modules; and wherein each of said plurality of lids comprises a pair of generally cylindrical hinge pins respectively disposed within said recesses of said pair of bosses of each respective lid hinge.

13. The first aid kit of claim 9 further comprising:

a plurality of lid hinges, each of said plurality of lid hinges having a generally planar tab with at least one rib thereon and a pair of generally cylindrical hinge pins extending from said tab;

wherein said at least one compartment of said first and second case modules has a slot for receiving a lid hinge, said at least one rib on said tab of each of said plurality of lid hinges being respectively disposed within said slot of said at least one compartment of said first and second case modules; and wherein each of said plurality of lids comprises a pair of bosses, each of said bosses having a generally cylindrical recess, wherein said hinge pins are respectively disposed within said recesses of said pair of bosses of each respective lid.

14. The first aid kit of claim 9 wherein at least one of said first and second case modules comprises an exterior wall for receiving a handle, said kit further comprising:

a handle having at least one probe traversing through said exterior wall of said case, said at least one probe having a catch for engaging a snap-in fastener; and at least one snap-in fastener having at least one prong engaged with said catch of said at least one probe to fasten said handle to said exterior wall.

15. The first aid kit of claim 9 further comprising at least one case hinge connecting said first case module and said second case module, said case hinge being fastened to said first and second case modules with fasteners having a plurality of barbs embedded within said foam of said first and second case modules.

16. The first aid kit of claim 9 wherein:
one of said first and second case modules has a peripheral protrusion having a semicircular cross-sectional shape with a radius of at least 1.5 mm;
the other of said first and second case modules has a peripheral recess having a semicircular cross-sectional shape with a radius of at least 1.5 mm; and
said peripheral protrusion mates with said peripheral recess to form a watertight seal.

17. The first aid kit of claim 9 wherein said kit is buoyant in water.

18. The first aid kit of claim 17 wherein said kit is capable of serving as a personal flotation device.

19. A first aid kit, comprising:
a first case module comprised of EPP foam having a density of about 70 grams/liter, said first case module having at least one compartment and a peripheral protrusion having a semicircular cross-sectional shape with a nominal radius of about 1.5 mm;
a second case module comprised of EPP foam having a density of about 70 grams/liter, said second case module having at least one compartment and a peripheral recess having a semicircular cross-sectional shape with a nominal radius of about 1.5 mm, said peripheral protrusion being slightly larger than said peripheral recess, wherein said peripheral protrusion mates with said peripheral recess to form a watertight seal;
a plurality of lids respectively covering said at least one compartment of said first and second case modules wherein each of said plurality of lids identifies a particular medical emergency, the particular medical emergency on each of said plurality of lids being different and being prioritized according to severity by ordered positional placement within said first and second case modules; and
medical supplies selectively contained within said at least one compartment of said first and second case modules for treating the particular medical emergency respectively identified on each of said plurality of lids.

20. The first aid kit of claim 19 further comprising at least one strap fastened to said first and second case modules with a plurality of fasteners, each of said plurality of fasteners having a plurality of barbs embedded within said foam of one of said first and second case modules.

21. The first aid kit of claim 19 further comprising at least one case hinge fastened to said first and second case modules with a plurality of fasteners, each of said plurality of fasteners having a plurality of barbs embedded within said foam of one of said first and second case modules.

22. The first aid kit of claim 19 wherein each of said plurality of lids has a bottom side bearing instructions concerning the use of said medical supplies for treating the particular medical emergency respectively identified on each of said plurality of lids.

23. The first aid kit of claim 19 wherein each of said plurality of lids bears a graphical illustration of the particular medical emergency respectively identified on each of said plurality of lids.

24. The first aid kit of claim 19 wherein said kit is buoyant in water.

25. The first aid kit of claim 19 wherein one of said first and second case modules comprises an exterior wall, said kit further comprising a handle having at least one probe traversing through said exterior wall, said at least one probe having a catch for engaging a snap-in fastener, and at least one snap-in fastener having at least one prong engaged with said catch to fasten said handle to said exterior wall.

26. The first aid kit of claim 19 wherein each of said plurality of lids is mounted to one of said first and second case modules with a lid hinge, said lid hinge having a generally planar tab with at least one rib thereon and a pair of bosses extending from said tab, each of said bosses having a generally cylindrical recess, said at least one rib being disposed within a slot in one of said first and second case modules, each of said plurality of lids having a pair of generally cylindrical hinge pins respectively disposed within said generally cylindrical recesses.

27. The first aid kit of claim 19 wherein each of said plurality of lids is mounted to one of said first and second case modules with a lid hinge, said lid hinge having a generally planar tab with at least one rib thereon and a pair of generally cylindrical hinge pins extending from said tab, said at least one rib being disposed within a slot in one of said first and second case modules, each of said plurality of lids having a pair of bosses, each of said bosses having a generally cylindrical recess, said hinge pins being respectively disposed within said generally cylindrical recesses.

* * * * *